United States Patent
Morrise et al.

(10) Patent No.: US 11,832,991 B2
(45) Date of Patent: Dec. 5, 2023

(54) AUTOMATIC ULTRASOUND FEATURE DETECTION

(71) Applicant: yoR Labs, Inc., Portland, OR (US)

(72) Inventors: Matthew C. Morrise, Portland, OR (US); Oliver C. Johnson-Terleski, Tualatin, OR (US)

(73) Assignee: yoR Labs, Inc., Beaverton, OR (US)

( * ) Notice: Subject to any disclaimer, the term of this patent is extended or adjusted under 35 U.S.C. 154(b) by 0 days.

(21) Appl. No.: 17/445,695

(22) Filed: Aug. 23, 2021

(65) Prior Publication Data

US 2022/0061814 A1    Mar. 3, 2022

Related U.S. Application Data

(60) Provisional application No. 63/070,224, filed on Aug. 25, 2020.

(51) Int. Cl.
*A61B 8/00* (2006.01)
*A61B 8/08* (2006.01)
(Continued)

(52) U.S. Cl.
CPC .............. *A61B 8/469* (2013.01); *A61B 8/463* (2013.01); *A61B 8/465* (2013.01); *A61B 8/5269* (2013.01);
(Continued)

(58) Field of Classification Search
CPC ......... A61B 8/469; A61B 8/463; A61B 8/465; A61B 8/5269; A61B 8/565; A61B 8/5223;
(Continued)

(56) References Cited

U.S. PATENT DOCUMENTS 4,998,132 A * 3/1991 Kurogane ................ H04N 1/46
399/182
5,617,371 A 4/1997 Williams
(Continued)

FOREIGN PATENT DOCUMENTS

AU    2018250516    11/2018
EP    2 288 284    5/2016
(Continued)

OTHER PUBLICATIONS

Bradley, Aug. 2008, Retrospective transmit beamformation: Acuson SC2000 volume imaging ultrasound system, Siemens Medical Solutions USA, Inc., whitepaper, 8 pp.
(Continued)

*Primary Examiner* — Yi-Shan Yang
*Assistant Examiner* — Alexei Bykhovski
(74) *Attorney, Agent, or Firm* — Knobbe, Martens, Olson & Bear, LLP

(57) ABSTRACT

Systems and methods for detecting features in ultrasound images and delineating boundaries that representative of the detected features. A method can include determining a boundary of a feature in a displayed ultrasound image, determining a closed polygon that represents the feature based on the boundary, and determining information of the feature using the dimensions of the closed polygon. The ultrasound image and graphical representations of the feature (e.g., the boundary, the closed polygon) can be displayed in a user interface on a touch screen display. The method can include receiving user input indicative of a location of the feature, and adjusting the feature boundary and closed polygon based on user input. The method can also include determining an area and/or a perimeter of the feature based on the closed polygon.

18 Claims, 8 Drawing Sheets

(51) Int. Cl.
*G06F 3/0488* (2022.01)
*G06T 7/73* (2017.01)
*G06T 5/00* (2006.01)
*G06T 11/20* (2006.01)

(52) U.S. Cl.
CPC ............ *A61B 8/565* (2013.01); *G06F 3/0488* (2013.01); *G06T 5/002* (2013.01); *G06T 7/73* (2017.01); *G06T 11/203* (2013.01); *G06T 2200/24* (2013.01); *G06T 2207/10132* (2013.01); *G06T 2207/20104* (2013.01)

(58) Field of Classification Search
CPC ...... G06F 3/0488; G06F 3/048; G06F 3/0481; G06F 3/04845; G06T 5/002; G06T 7/73; G06T 11/203; G06T 2200/24; G06T 2207/10132; G06T 2207/20104; G06T 2207/20096; G06T 2207/30048; G06T 7/62
See application file for complete search history.

(56) References Cited

U.S. PATENT DOCUMENTS

| | | |
|---|---|---|
| 5,903,516 A | 5/1999 | Greenleaf et al. |
| 5,908,389 A | 6/1999 | Roundhill et al. |
| 6,031,529 A | 2/2000 | Migos |
| 6,063,030 A | 5/2000 | Vara et al. |
| 6,120,450 A | 9/2000 | Li |
| 6,123,670 A | 9/2000 | Mo |
| 6,132,374 A | 10/2000 | Hossack et al. |
| 6,400,981 B1 | 6/2002 | Govari |
| 6,607,489 B2 | 8/2003 | Hoctor |
| 6,690,963 B2 | 2/2004 | Haim et al. |
| 6,908,434 B1 | 6/2005 | Jenkins et al. |
| 7,090,639 B2 | 8/2006 | Govari |
| 7,423,578 B1 | 9/2008 | Tietjen |
| 7,604,601 B2 | 10/2009 | Altmann et al. |
| 7,648,462 B2 | 1/2010 | Jenkins et al. |
| 7,667,639 B2 | 2/2010 | Cheng et al. |
| 7,682,358 B2 | 3/2010 | Gullickson et al. |
| 7,750,849 B2 | 7/2010 | Hjelmstad |
| 7,831,076 B2 | 11/2010 | Altmann et al. |
| 7,860,553 B2 | 12/2010 | Govari et al. |
| 7,918,793 B2 | 4/2011 | Altmann et al. |
| 7,996,060 B2 | 8/2011 | Trofimov et al. |
| 8,075,486 B2 | 12/2011 | Tal |
| 8,285,364 B2 | 10/2012 | Barbagli et al. |
| 8,390,438 B2 | 3/2013 | Olson et al. |
| 8,449,467 B2 | 5/2013 | Wilser et al. |
| 8,517,946 B2 | 8/2013 | Kim |
| 8,676,290 B2 | 3/2014 | Tegg |
| 8,690,871 B2 | 4/2014 | Partlett et al. |
| 8,702,612 B2 | 4/2014 | Hendriks et al. |
| 8,989,842 B2 | 3/2015 | Li et al. |
| 9,030,354 B2 | 5/2015 | Natarajan |
| 9,055,883 B2 | 6/2015 | Tgavalekos et al. |
| 9,095,682 B2 | 8/2015 | Romoscanu |
| 9,132,913 B1 | 9/2015 | Shapiro et al. |
| 9,179,890 B2 | 11/2015 | Ionasec et al. |
| 9,211,160 B2 | 12/2015 | Pivotto et al. |
| 9,261,595 B2 | 2/2016 | Garbini et al. |
| 9,323,445 B2 | 4/2016 | Kritt et al. |
| 9,342,156 B2 | 5/2016 | Huh |
| 9,922,554 B2 | 3/2018 | Mikuni et al. |
| 9,931,487 B2 | 4/2018 | Quinn et al. |
| 9,986,969 B2 | 6/2018 | Call et al. |
| 10,183,149 B2 | 1/2019 | Tegg et al. |
| 10,206,652 B2 | 2/2019 | Deno et al. |
| 10,368,951 B2 | 8/2019 | Moll et al. |
| 10,401,492 B2 | 9/2019 | Brooks |
| 10,405,830 B2 | 9/2019 | Garbini et al. |
| 10,463,439 B2 | 11/2019 | Joseph et al. |
| 10,499,882 B2 | 12/2019 | Hunter et al. |
| 10,537,307 B2 | 1/2020 | Yang |
| 10,555,780 B2 | 2/2020 | Tanner et al. |
| 10,624,612 B2 | 4/2020 | Sumi |
| 11,344,281 B2 | 5/2022 | Morisse et al. |
| 11,547,386 B1 | 1/2023 | Roy et al. |
| 2002/0173721 A1 | 11/2002 | Grunwald |
| 2002/0173722 A1 | 11/2002 | Hoctor et al. |
| 2003/0007598 A1 | 1/2003 | Wang et al. |
| 2003/0055334 A1 | 3/2003 | Steinbacher et al. |
| 2003/0055337 A1 | 3/2003 | Lin |
| 2004/0102700 A1 | 5/2004 | Asafusa |
| 2005/0288588 A1 | 12/2005 | Weber et al. |
| 2007/0027733 A1 | 2/2007 | Balle |
| 2007/0174772 A1 | 7/2007 | Gorman |
| 2007/0200760 A1 | 8/2007 | Hjelmstad |
| 2007/0239001 A1 | 10/2007 | Mehi et al. |
| 2007/0259158 A1 | 11/2007 | Friedman et al. |
| 2008/0012753 A1 | 1/2008 | Cheng |
| 2008/0114239 A1 | 5/2008 | Randall et al. |
| 2008/0215046 A1 | 9/2008 | Messing et al. |
| 2008/0306385 A1 | 12/2008 | Jago |
| 2009/0043206 A1 | 2/2009 | Towfiq et al. |
| 2009/0118620 A1 | 5/2009 | Tgavalekos et al. |
| 2009/0271704 A1 | 10/2009 | Cohen |
| 2010/0030076 A1 | 2/2010 | Vortman et al. |
| 2010/0081938 A1 | 4/2010 | Kato |
| 2010/0146431 A1 | 6/2010 | Raji et al. |
| 2010/0160784 A1 | 6/2010 | Poland |
| 2010/0168580 A1 | 7/2010 | Thiele |
| 2010/0251823 A1 | 10/2010 | Adachi |
| 2011/0077524 A1 | 3/2011 | Oshiki et al. |
| 2011/0137132 A1 | 6/2011 | Gustafson |
| 2011/0208052 A1 | 8/2011 | Entrekin |
| 2012/0075208 A1 | 3/2012 | Tamiya et al. |
| 2012/0157851 A1 | 6/2012 | Zwirn |
| 2012/0254747 A1* | 10/2012 | Bocirnea ................ G16H 30/40 345/620 |
| 2013/0227052 A1 | 8/2013 | Wenzel |
| 2013/0234891 A1 | 9/2013 | Natarajan et al. |
| 2013/0238990 A1 | 9/2013 | Ubillos et al. |
| 2013/0253317 A1 | 9/2013 | Gauthier |
| 2013/0274712 A1 | 10/2013 | Schecter et al. |
| 2013/0310690 A1* | 11/2013 | Chang ................ A61B 8/085 600/443 |
| 2014/0035916 A1 | 2/2014 | Murphy |
| 2014/0046188 A1 | 2/2014 | Yen et al. |
| 2014/0058266 A1 | 2/2014 | Call et al. |
| 2014/0087342 A1 | 3/2014 | Campanatti, Jr. |
| 2014/0164965 A1 | 6/2014 | Lee et al. |
| 2014/0189560 A1 | 7/2014 | Caspi |
| 2014/0219059 A1 | 8/2014 | Younghouse |
| 2015/0019488 A1 | 1/2015 | Higginson et al. |
| 2015/0065877 A1 | 3/2015 | Orderud |
| 2015/0082251 A1 | 3/2015 | Lam |
| 2015/0293223 A1 | 10/2015 | Park et al. |
| 2016/0054901 A1* | 2/2016 | Yang ................ A61B 8/464 600/443 |
| 2016/0157824 A1 | 6/2016 | Park et al. |
| 2016/0161589 A1 | 6/2016 | Benattar |
| 2016/0161594 A1 | 6/2016 | Benattar |
| 2016/0161595 A1 | 6/2016 | Benattar |
| 2016/0165338 A1 | 6/2016 | Benattar |
| 2016/0165341 A1 | 6/2016 | Benattar |
| 2016/0338676 A1 | 11/2016 | Berger et al. |
| 2017/0090571 A1* | 3/2017 | Bjaerum ............... A61B 8/4254 |
| 2017/0153801 A1 | 6/2017 | Kim et al. |
| 2017/0307755 A1 | 10/2017 | Brooks |
| 2017/0343655 A1 | 11/2017 | Solek et al. |
| 2017/0343668 A1 | 11/2017 | Brooks et al. |
| 2018/0000449 A1 | 1/2018 | Moore et al. |
| 2018/0000453 A1 | 1/2018 | Hunter et al. |
| 2018/0055483 A1 | 3/2018 | Hunter |
| 2018/0064415 A1 | 3/2018 | Zhai et al. |
| 2018/0361145 A1 | 12/2018 | Mahapatra et al. |
| 2019/0245310 A1 | 8/2019 | Medina et al. |
| 2019/0261953 A1 | 8/2019 | Honjo et al. |
| 2019/0307427 A1* | 10/2019 | Levy ................... A61B 6/5217 |
| 2019/0324139 A1 | 10/2019 | Brooks |
| 2019/0353975 A1 | 11/2019 | DiDomenico |
| 2020/0046321 A1 | 2/2020 | Duda |

(56) References Cited

U.S. PATENT DOCUMENTS

| | | |
|---|---|---|
| 2020/0060646 A1 | 2/2020 | Lindenroth et al. |
| 2020/0170662 A1 | 6/2020 | Vardi |
| 2020/0178928 A1 | 6/2020 | Park et al. |
| 2020/0183004 A1 | 6/2020 | Gong et al. |
| 2020/0205783 A1 | 7/2020 | Shiran |
| 2020/0268351 A1 | 8/2020 | Chiang |
| 2020/0281565 A1 | 9/2020 | Yee et al. |
| 2020/0315592 A1 | 10/2020 | Soleimani et al. |
| 2021/0007710 A1* | 1/2021 | Douglas ............... A61B 8/4245 |
| 2021/0038334 A1 | 2/2021 | Hsu et al. |
| 2021/0125503 A1* | 4/2021 | Henry .................... G05D 1/106 |
| 2021/0177379 A1 | 6/2021 | Kolen et al. |
| 2021/0338208 A1 | 11/2021 | Nguyen et al. |
| 2021/0401508 A1 | 12/2021 | Zhao |
| 2022/0061811 A1 | 3/2022 | Terleski |
| 2022/0151591 A1 | 5/2022 | Morrise |
| 2022/0156094 A1 | 5/2022 | Morrise |
| 2023/0059122 A1 | 2/2023 | Pellegrino |

FOREIGN PATENT DOCUMENTS

| | | |
|---|---|---|
| EP | 3 275 478 | 1/2018 |
| EP | 2 707 076 | 11/2018 |
| EP | 3 050 214 | 3/2019 |
| EP | 2 632 318 | 11/2019 |
| EP | 3 518 777 | 3/2021 |
| WO | WO 12/088535 | 6/2012 |
| WO | WO 20/049012 | 3/2020 |
| WO | WO 20/252416 | 12/2020 |

OTHER PUBLICATIONS

Lin et al., Jun. 2010, A motion compounding technique for speckle reduction in ultrasound images, Journal of digital imaging 23(3):246-257.

* cited by examiner

- Identified Feature

- Draw Shape around Feature

*- Examine Detected Boundary*

*- Adjust Boundary*

– Convert Boundary to Polygon

– Add Polygonal Line to Edit Polygon

- Final Polygon with Area and Perimeter Automatically Calculated

AUTOMATIC ULTRASOUND FEATURE DETECTION

BACKGROUND OF THE INVENTION

Field

This disclosure relates to detecting an object in an image. Specifically, this disclosure relates to detecting a feature in an ultrasound image.

Description of the Related Art

Ultrasound imaging is used in the diagnosis, screening, and treatment of a variety of diseases and conditions. An ultrasound image is created by transmitting sound waves into the body and then interpreting the intensity of the reflected echoes. The echoes are commonly used to produce two dimensional, three-dimensional, and color flow images of internal anatomical objects of patients.

When an object of interest is identified in an ultrasound image (a "target object" or "feature"), information about the feature can be collected and used for further analysis, for example, in a protocol. The information about the feature may include the area of the feature and/or the perimeter of the feature, and other characteristics determinable from the ultrasound image. Although some tools may be available to help the user estimate information about the feature, it would be advantageous for the ultrasound system to have functionality that would automatically determine information about the feature, or determine information about the feature with minimal user interaction/input.

SUMMARY

Provided herein is a system and method for determining information about features of interest in ultrasound images, either automatically or with minimal user interaction. Two methods of identifying features in ultrasound images are (i) drawing an ellipse of the approximate size of a feature, and (ii) drawing a free form polygon to approximate the feature. Automatically detecting the shape of the feature can be done by providing an input indicative of the location, or a shape around the location, of a feature (for example, an ellipse or free form polygon around the feature), and then filtering pixels in the proximity of the indicating location, or inside the drawn shape, to determine the feature boundary. The feature determination can be at least partially based on pixel brightness on the displayed ultrasound image that contains the feature. In some embodiments, user controls allow the feature to be expanded/contracted by adjusting the brightness, contrast, or another image processing control (e.g., histogram equalization). In various embodiments, both dark features and bright features can be detected. After boundary of the feature has been determined, information relating to the dimensions of the feature may be calculated based on the boundary for example, two important values that can be determined based on the feature boundary area and perimeter. In some embodiments, the volume of the feature may also be determined (or estimated). The boundary of the feature may be smoothed before information of the feature is calculated, for example, by using cubic splines and/or by removing points on the boundary.

One innovation is a method of detecting features in ultrasound images and determining a graphical representation of the feature that can be used to determine information about the feature, the method including determining a boundary of a feature in a displayed ultrasound image, determining a closed polygon that represents the feature based on the boundary, and determining information of the feature using the dimensions of the closed polygon, wherein the method is performed by one or more computer hardware processors configured to execute computer-executable instructions stored on a non-transitory computer storage medium.

In various embodiments, the method may include one or more other features, as indicated in the following non-limiting examples. For example, a method may further include receiving user input indicative of a location of the feature, wherein determining the boundary is based on the user input. A method may further include receiving the user input indicative of the location of the feature comprises receiving a signal from a touchscreen display, that is displaying the ultrasound image, as a result of a user touch of the touchscreen. Receiving the user input indicative of the location of the feature can include receiving a signal from one of a mouse, trackball, or a keyboard. A method may further include performing automatic feature detection on the ultrasound image to determine a location of the feature, wherein determining the boundary is based on the determined location. The automatic feature detection can be at least partially based on intensity of pixels in the ultrasound image. A method may further include adjusting the feature boundary by changing at least one of brightness or contrast of the displayed ultrasound image. A method may further include adjusting a portion of the boundary, based on user input, to form an adjusted boundary, and wherein determining the closed polygon that represents the feature is based on the adjusted boundary. In some methods, adjusting a portion of the boundary, based on user input comprises receiving a signal, from a touchscreen displaying the ultrasound image and the boundary, indicative of a point on the ultrasound image, and adjusting a portion of the boundary adjacent to the point to move the boundary away from the point. In some methods, adjusting a portion of the boundary, based on user input comprises receiving a signal, from a touchscreen displaying the ultrasound image and the boundary, indicative of a point on the ultrasound image, and adjusting a portion of the boundary adjacent to the point to move the boundary towards from the point. A method may further include editing the polygon. In some methods, editing the polygon comprises receiving user input indicating a first point of the polygon and a second point of the polygon, defining a new line between the first point and the second point, and replacing the portion of the polygon between the first and second point with the new line between the first and second point. A method may further include smoothing the feature boundary. In some methods the boundary is smoothed using cubic splines or by removing points of the boundary. In method may further include smoothing the closed polygon. In some methods, the closed polygon is smoothed using cubic splines or by removing points of the polygon. In some methods, determining information of the feature using the dimensions of the closed polygon comprises determining one or more of the area of the closed polygon, the perimeter of the closed polygon, or the volume of the closed polygon. A method may further include generating a feature detection user interface comprising the ultrasound image and graphical representations, the graphical representations comprising the boundary and the closed polygon, and causing presentation of the feature detection user interface on a touchscreen display.

Another innovation is a system for detecting features and ultrasound image. The feature may be identified by a user input indicating the feature on a portion of a displayed ultrasound image on a touchscreen display interface. A feature location may be indicated by a user selecting a point on the image that is contained in the feature, or by indicating an area on the image surrounding the feature. For example, by indicting a minimum bounding rectangle around the feature, by indicating a circle or an ellipse around the feature, or by indicating the edges of the feature (e.g., drawing a polygon that approximates edges of the feature). Once the location of the feature has been indicated, the process may perform automatic feature detection to generate a graphical representation of the shape (or boundary) of the feature, and display the representation overlaid on the ultrasound image that contains the feature. A user may examine the feature boundary and adjust the boundary to better represent the feature in the ultrasound image. The process may convert the boundary to polygon, and provide functionality to a user to allow the user to edit the polygon to match the area and/or the perimeter of the feature. In one example, such a system can include an ultrasound probe, an ultrasound processing system including a wireless network communication interface connecting the ultrasound probe to the processing for receiving ultrasound data from the ultrasound probe and for providing control information to the ultrasound probe, a first non-transitory computer storage medium configured to store ultrasound data provided by the ultrasound probe, second non-transitory computer storage medium configured to at least store computer-executable instructions, and one or more computer hardware processors in communication with the second non-transitory computer storage medium. The one or more computer hardware processors configured to execute the computer-executable instructions to at least receive user input indicative of a location of the feature, generate a feature detection user interface, the feature detection user interface comprising the ultrasound image and one or more graphical representations of the feature, and cause presentation of the feature detection user interface on a touchscreen display, determine a boundary of a feature in a displayed ultrasound image based on the user input, adjust the feature boundary based on user input indicative of moving a portion of the boundary, determine a closed polygon that represents the feature based on the boundary, edit the closed polygon based on user input indicating a first point of the polygon and a second point of the polygon, the first and second point defining a new line between the first point and the second point to replace the portion of the polygon between the first and second point with the new line between the first and second point, and determine information of the feature using the dimensions of the closed polygon.

In various embodiments, the system may include one or more other features, as indicated in the following non-limiting examples. In one example of such systems, the determined information comprises at least one of the area of the closed polygon, the perimeter of the closed polygon, or the volume of the closed polygon. Receiving user input indicative of the location of the feature can include receiving a signal from a touchscreen display, that is displaying the ultrasound image, as a result of a user touch of the touchscreen. Receiving the user input indicative of the location of the feature can include receiving a signal from one of a mouse, trackball, or a keyboard. A system can be further configured such that the one or more computer hardware processors are further configured to execute the computer-executable instructions to perform automatic feature detection on the ultrasound image, based on the user input, to determine a location of the feature, wherein the boundary is based on the determined location. The automatic feature detection can be at least partially based on intensity of pixels in the ultrasound image. The one or more computer hardware processors can be further configured to adjust the feature boundary by changing at least one of brightness or contrast of the displayed ultrasound image. The one or more computer hardware processors can be further configured to adjust a portion of the boundary, based on user input, to form an adjusted boundary, and the determined closed polygon is based on the adjusted boundary. The one or more computer hardware processors can be further configured to adjust a portion of the boundary based on user input, from a touchscreen displaying the ultrasound image and the boundary, indicative of a point on the ultrasound image, and adjust a portion of the boundary adjacent to the point to move the boundary away from the point. The one or more computer hardware processors can be further configured to adjust a portion of the boundary based on user input, from a touchscreen displaying the ultrasound image and the boundary, indicative of a point on the ultrasound image, and adjust a portion of the boundary adjacent to the point to move the boundary towards the point. In some systems, the one or more computer hardware processors are further configured to edit the polygon based on user input. In some systems the one or more computer hardware processors are further configured to receive user input indicating a first point of the polygon and a second point of the polygon, define a new line between the first point and the second point, and replace the portion of the polygon between the first and second point with the new line between the first and second point. In some systems, the one or more computer hardware processors are further configured to smooth the feature boundary. The one or more computer hardware processors can be further configured to smooth the boundary using cubic splines or by removing points of the boundary. In some systems, the one or more computer hardware processors are further configured to smooth the closed polygon. In some systems, the one or more computer hardware processors are further configured to smooth the closed polygon using cubic splines or by removing points of the polygon.

DETAILED DESCRIPTION

Overview

Figure 1:
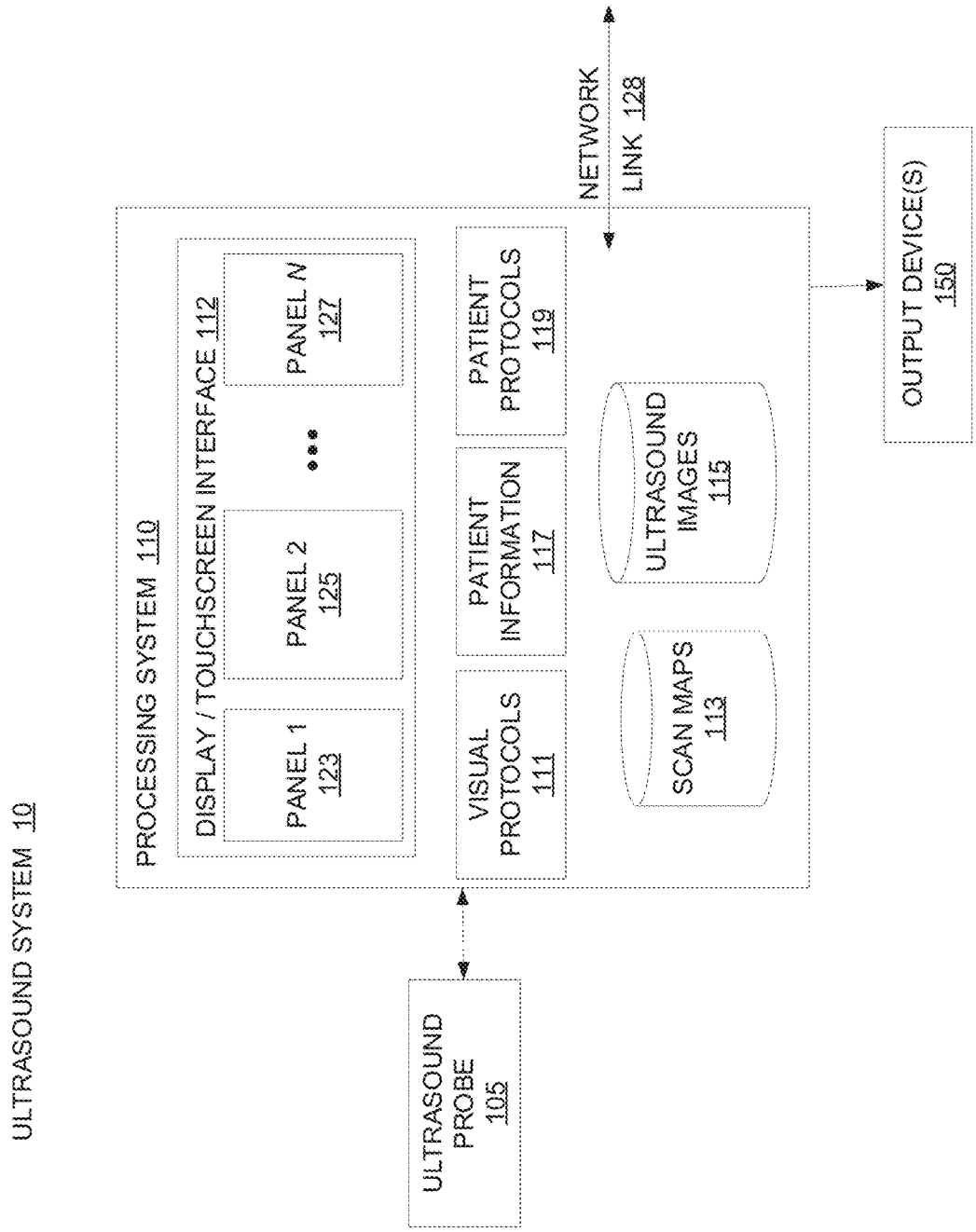
FIG. 1 is a block diagram illustrating an example of an ultrasound system that can be used to perform automatic feature extraction on ultrasound images.

Embodiments of systems and methods for performing feature detection are disclosed herein. A software application provides a user interface for selecting, visualizing, and interacting with ultrasound images, including detecting features in an ultrasound image, and determining information relating to the features. For example, a method may include determining a boundary of a feature in a displayed ultrasound image, determining a closed polygon that represents the feature based on the boundary, and determining information of the feature using the dimensions of the closed polygon. The method may also include adjusting the boundary of the feature, and/adjusting the closed polygon that represents a boundary of the feature.

To identify location of feature in an ultrasound image, the user may use a touchscreen display is displaying the ultrasound image containing the feature, to indicate an area in the ultrasound image where the feature located. For example, by drawing an ellipse or a minimum body rectangle around a portion of the ultrasound image containing the feature. Based on pixel intensity and image processing techniques, initial boundary of the feature may be determined and displayed to the user on the touchscreen display. The user may adjust the initial boundary to better represent the boundaries of the feature. For example, the user may move the boundary, or adjust the image such that the system can better determine the boundary of the feature. A closed polygon representative of the boundaries of the feature can be generated, and the closed polygon may be further adjusted by a user, if necessary. When the user satisfied with the polygon has been representative of the feature, the polygon can be used to determine the area and the perimeter of the feature, and this information may be saved, for example, in association with a visual protocol been performed or another analysis that the user is performing.

Terms

In order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

"Database" in this context refers to an organized collection of data (states of matter representing values, symbols, or control signals to device logic), structured typically into tables that comprise 'rows' and 'columns.'

"Final Report" in this context refers to the final product of an ultrasound scan including written documentation of the imaging findings and an impression or diagnosis based on those findings.

"Graphical representation" in this context refers to a stylized drawing of the body part being scanned.

A "loop", "cineloop", "time-lapse", or "video loop" in this context may be used interchangeably to refer to a time series of images. In some embodiments, a 4D image may be a time-lapse of 3D image(s). In other embodiments, individual frames can be sequenced to form a video loop.

"Module" in this context refers to logic having boundaries defined by function or subroutine calls, branch points, application program interfaces, or other technologies that provide for the partitioning or modularization of particular processing or control functions. Modules are typically combined via their interfaces with other modules to carry out a machine process.

"Protocol" in this context refers to a written outline, checklist, or worksheet that list images and measurements that should be acquired during the specified ultrasound examination.

"Reader" in this context refers to the person interpreting the ultrasound scan.

A "scanner" or "ultrasound device" in this context refers to a device for performing ultrasound imaging (sonography), which uses high-frequency sound waves to examine an object. The device may comprise an ultrasonic transducer or an ultrasonic transducer array used to probe the object. Transducers may be part of a sequential array in which the acoustic beam is focused straight in front of the transducer, providing high sensitivity but a limited field of view, or a phased array in which each transducer sends an acoustic beam in a coordinated sequence, establishing a pattern of constructive interference that results in a beam at a set angle, allowing for a wider field of view. Phased array transducers may comprise multiple transducer elements which may be arranged in a variety of shapes including a strip (linear array), a ring (annular array), a circular matrix (circular array), conformal array, curved, or a more complex shape. A "scanner" used herein may be hand-held or portable.

"Ultrasound study" in this context refers to a diagnostic procedure performed by a sonographer that uses two-dimensional images produced by inaudible sound waves to evaluate an anatomical feature.

"User" in this context refers to the person performing an ultrasound scan. "Reader" in this context refers to the person interpreting an ultrasound scan. A "sonographer" may both perform and interpret an ultrasound scan.

"Scan plane" in this context refers to the orientation of the ultrasound probe relative to the part being scanned.

When 3D imaging is available, ultrasound viewing and saving may include three modes: scanning, frozen, and review. "Scanning" in this context refers to showing images directly from the scanner (e.g., the ultrasound device). "Frozen" in this context refers to showing the last N seconds of images from the scanner. "Review" in this context refers to showing images that are explicitly saved.

A "frame" in this context is for specifying the space and time aspect of an image. In other words, a frame is the image at a given position with respect to the time the image was taken. In some embodiments, a "frame" may be a 2D image. In other embodiments, when a user is performing the 3D imaging mode via an ultrasound device, a "frame" may additionally cover each image taken by the ultrasound device in that same instance.

"Scan plane" in this context refers to the orientation of the ultrasound probe relative to the part being scanned.

"Structured labels" in this context refers to a list of labels used for a specific exam type in which the labels are automatically presented in a set order.

"Slices": Bundled images in frozen and review modes are called a "capture" and there are four types of capture: 2D image, 2D series (cineloop), 3D image, and 3D series (3D cineloop). The information (or image data) that constitute ultrasound 3D image captures are called "slices". A "slice" in this context may be a thin 3D composite image formed from a collection of 2D images.

A "thick slice mode" in this context refers to a 3D image taken by an ultrasonic transducer array. A "tomography" in this context refers to a time series of 2D or 3D images taken by an ultrasonic transducer array is in motion relative to the object being scanned.

"Touch screen" in this context refers to a capacitive or resistive display which responds to direct touch manipulation, either by finger (simple or multi-touch), stylus, or both. The user can use the touch-screen to react to what is displayed and to control how it is displayed. The touch-screen enables the user to interact directly with information displayed rather than using a mouse, touchpad, or other intermediate device (with the exception of a stylus).

"Ultrasound study" in this context refers to a diagnostic procedure performed by a sonographer that uses two-dimensional images produced by inaudible sound waves to evaluate an anatomical feature.

"User" in this context refers to the person actually performing the ultrasound scan.

"Visual Protocol" in this context refers to a protocol that is displayed on a display screen of a computer system, and that is updated based on a user's interactions. The visual protocol can associate a protocol checklist with a diagram of a scan map (a diagram of the scanned body part). The visual protocol can also associate the protocol checklist with a textual list of annotations for the image and a series of thumbnail images (a "gallery"), where each of the thumbnail images is associated with a full-size ultrasound image that can be when the thumbnail image is selected. The visual protocol can also associate the protocol checklist with measurements that are to be acquired during the specified ultrasound examination.

"Word bank" in this context refers to a list of context-specific labels which are commonly used for a specific scan type or body part.

"Worksheet" in this context refers to a generated document comprising patient information, scan information, and images and written findings from the ultrasound.

Data Representation

In some embodiments, the data representation of a scanned image may be able to represent all the needed fields to both display and to signify the exact display variant the renderer should use. Additionally, the data format may be flexible enough to allow for transformations to other supported display variants if possible.

The data implementation may represent a single slice or a single frame, or captures which are collections of images along with other properties. Checking the contents of captures allows for explicitly knowing the type of scan and variant needed to display. Knowing this type then specifies all actions that can be taken on the capture, as well as directing the display renderer how it should render the image data.

An image may be a single frame or a single slice. In some embodiments, image data that is saved to the database for an individual image may include the following immutable fields:
(1) Raw pixel data for what was imaged.
(2) Depth details to specify constraint of bottom of image. The depth refers to a 2D image's y-axis which corresponds to how deep the scanner is imaging.
(3) Timestamp to have relative timing information relative to other image data
(4) Relative position data in x, y, and z directions.
(5) Relative angle position data in x, y, and z directions.
(6) Relative slice position and total number of slices for beamformed 3D image if applicable.

Bundled images in frozen and review modes are called a capture. A capture may be a 2D image, a 2D series (cineloop), a 3D image, or a 3D series (3D cineloop). A capture may include multiple frames and/or slices, where the multiple frames may include images that are changing in time, and multiple slices may include images that are changing spatially. A capture may be the full collection of the images taken over both time and space. Different capture types represent different display variants, including:

A "frame", which is a single image at a given time point.

A "loop", which include multiple images focused on essentially the same spatial area but changing in time.

A "slice", which includes images of a spatial range near a spatial position. Multiple slices are used to create a 3D image.

A "2D time-lapse" or a 3D "time-lapse", which includes images taken in the same location over a time range.

A "thick slice", which includes images taken in 3D mode in a stable location with a given spatial and time sampling rate.

A "tomography", which includes images taken while traversing (moving the scanning probe) a region that is both time and spatially variant.

A "loop", which is a time series of data. The spatial information can be rendered in 3D or as a 2D plane. As each image data has time and spatial information, projections between the different dimensions can be made.

Example System

FIG. 1 is a block diagram illustrating an example of an ultrasound system 10 for processing and analyzing ultrasound images, including feature extraction. For example, the ultrasound system 10 can be used to complete a visual protocol. The ultrasound system 10 can also be used to detect a feature in an ultrasound image, generate graphical representations of a feature, and determine information about the feature. The functionality described in FIGS. 2-10 relating to feature detection and generating graphical representations of features found in ultrasound images may be included as a tool, or a set of tools, in a system that is configured to complete the visual protocol. For example, when performing a visual protocol on a patient, feature detection functionality may be used to detect the boundaries of a feature, generate graphical representation of the feature, and determine information about the feature (e.g., the area, perimeter, and/or volume of the feature).

The ultrasound system 10 includes an ultrasound probe 105 that communicates with a processing system 110. The ultrasound probe 105 can be a handheld ultrasound device that comprises a transducer array configured to transmit an ultrasound signal to a target object, receive an ultrasound echo signal reflected from the target object, and form ultrasound data corresponding to the target object. The processing system 110 can be any type of computer device (e.g., a desktop computer, a tablet, a laptop, or another mobile device) that is suitably configured to perform visual protocols. The ultrasound probe 105 can be controlled by the processing system 110 to provide ultrasound images to the processing system 110.

The processing system 110 can include a display/touchscreen interface 112 ("interface") that can display a visual protocol, ultrasound images, measurement information and other information related to the visual protocol in one or more panels 123, 125, and 127. In some preferred embodiments, the display screen and the user interface are implemented together such that most, or all, of the controls to complete the visual protocol are available on the interface 112, but some systems may have a separate display and interface. The interface can be any type of a flat screen, LED screen, electroluminescent display, organic LED, LCD, virtual display and the like that can display information and receive input from a user in the directly to the display or to another device that is in communication with the display. The processing system 110 may also include voice recognition to manipulate information and/or images on the interface 112. In various embodiments, controls that allow a user to perform feature detection may be employed in any panel on the interface 112. In some embodiments, the interface 112 includes a control that when invoked by user input, causes the display of feature detection tools.

The interface 112 may present information in a variety of ways. In some embodiments, the interface 112 is divided into a plurality of panels (or sectors) 123, 125, and 127 in any order, each of which may contain one or more of: a visual protocol, patient information, an active ultrasound image being currently acquired from a machine transformation of an ultrasound reading in process (active scan), thumbnails of ultrasound images from the current exam, and thumbnails of recorded images from a previous exam. In some embodiments, the thumbnails may be presented in chronological order. In other embodiments, the thumbnails may be presented in an order chosen by the user. Each thumbnail image may be expanded, moved, or removed as desired using gestures on the user interface. In some embodiments, the thumbnails may be stacked one on top of each other with the most recent scan on top. In other embodiments, thumbnails may be presented in discrete rows. Thumbnails may be labeled with the date and time of the scan as well as any other relevant label or descriptive information including, but not limited to, patient information, scan location, scan date, scan plane, anatomical subject of the scan, presence or absence of lesions, purpose of the scan, measurements of lesions, number of lesions and the like. As described in more detail in reference to FIG. 3, the interface 112 can display information related to a visual protocol or feature detection being performed and receive user input via its touchscreen functionality, or other input devices (e.g., keyboard, mouse, and the like) that are in communication with the processing system 110.

Performing a visual protocol and/or feature detection may generally include, for example, selecting a visual protocol to perform, associating the visual protocol and the ultrasound images with a patient, and receiving ultrasound images from the ultrasound probe 105. Performing the visual protocol may also include recording, associating, measuring comparing, labeling, reporting and/or documenting information (features) in images received from the ultrasound probe 105. The plurality of panels 123, 125, and 127 on the interface 112 allow for the display of the visual protocol, interaction with one or more ultrasound images and graphical representations, and measurement of objects depicted in ultrasound images. The processing system 110 may include various modules to facilitate the completion of the feature extraction. For example, the processing system 10 may include a measurement module activated by the user interface to determine appropriate measurements of a feature in a displayed ultrasound image (e.g., of an objected visible in an ultrasound image) and to generate a graphical representation of the measurement on a target object. The processing system 110 may also include a labeling module activated by the user interface to add the appropriate labels to the active ultrasound image and to a graphical representation of the target object. The processing system 110 may include a computer visualization application operated via the user interface for the display of the visual protocol, ultrasound images associated with the visual protocol, and measurements and labels associated with the visual protocol.

The processing system 110 may store information that is used to perform feature extraction and visual protocols. For example, the processing system 110 may store one or more of visual protocols 111, patient information 117, scan maps 113, ultrasound images 115 (e.g., that are either generated during the exam or are from previous exams), and completed patient protocols 119. In some embodiments, one or more of the visual protocols, scan maps, patient information, ultrasound images, and completed patient protocols are stored on a system that is in communication with the processing system 110 via a network link 125. For example, because of the potentially large size of the images that may be collected while performing a visual protocol, at least some of the ultrasound images that are collected may be stored on a high-speed computer storage device is in communication with the processing system 110 via the network link 125. The processing system 110 may also include one or more output devices 150 that can be used to, for example, generate a report or provide the visual protocol "package" having information and images that is stored and subsequently used for further analysis of a patient.

The visual protocols 111 may include information that is required to complete a particular visual protocol. For example, a list of steps to complete, images of certain anatomy that are needed, features to detect, measurements that are needed, and criteria (e.g., size) relating to objects in the ultrasound images that indicate that additional information images or steps are needed if the objects meet the particular criteria. Steps of a visual protocol can be displayed on the interface 112, a step can be selected, and information (e.g., images, measurements, annotations) needed to complete the step is displayed. A user can then quickly and efficiently provide input to the interface 112 to display and indicate to associate one or more images with the step, perform measurements required for the step, and provide annotations as required by each step of the visual protocol.

As mentioned above, the interface 112 may be a combination display and touch screen that allows the user to manipulate the images on the display. Touch-screen based computers comprise computer assemblies combining an internal computer processor and touch sensitive digital display screen. The display and the computer's ability to monitor the positions and motions of finger touches on the touch-screen are coordinated such that finger contact locations can be correlated by the computer with the information displayed at those locations. A variety of gestures may be used to interact with the interface 112, including, but not limited to, touching, swiping, double tap, multiple finger taps, pinch, multi-touch, radio buttons and the like. A processor is coupled to the touch-screen for detecting a touch by the user on the touch-screen that identifies a selected activation area. The processor then performs the device function associated with the stored image manipulation function thereby activating the selected activation area. In some embodiments, the user may interact with the interface 112 through voice recognition, a stylus, keyboard, mouse, virtual reality headset, hand gestures in the air, any other way generally used to interact with a user interface, or a combination thereof. In some embodiments, controls on the ultrasound probe 105 may be used to input information onto either or both the interface 112.

The interface 112 can be divided into a plurality of control panels including, but not limited to, a proportionate graphical representation of the anatomical part being scanned, a scale or other measuring apparatus, a track pad, a series of one or more virtual controls such as buttons or radio buttons, word bank, structured label bank, tabbed drop down menus, virtual keyboard, active ultrasound image, virtual trackpad, virtual depth and focus sliders, virtual cine slider, and virtual time gain compensation sliders that can be used for feature detection. In some embodiments, the number and arrangement of control panels may be altered to suit the needs of the user. For example, during a scan, it may be desirable to have an extended display of one or more of the control panels. In some embodiments, there may be one control panels. In other embodiments, there may be 2, 3, 4, 5, 6, 7, 8, 9, 10, 11, 12 or more control panels. Activation of each panel on the interface 112 may perform a function on interface 112 and can manipulate information on the interface 112.

Figure 2:
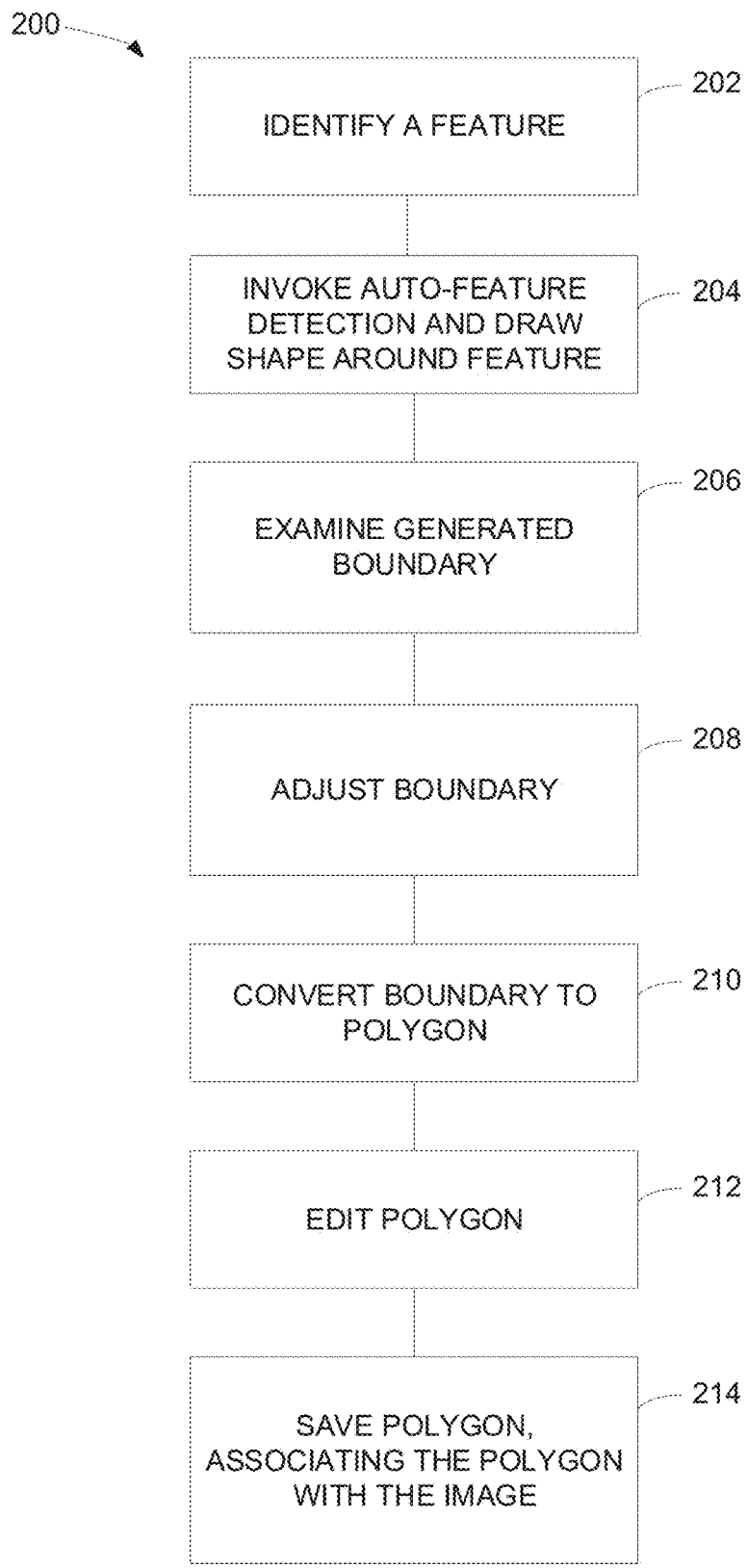
FIG. 2 is a flow chart that illustrates an example of a process for performing feature extraction, which can be performed on the ultrasound system illustrated in FIG. 1.
Figure 4:
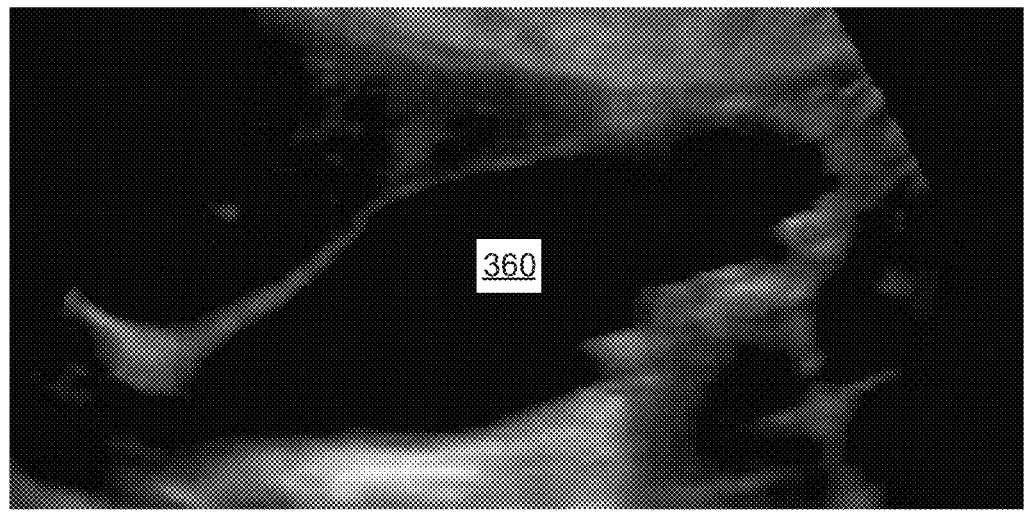
FIG. 4 illustrates an example of a displayed ultrasound image depicting an example of a target feature.
Figure 5:
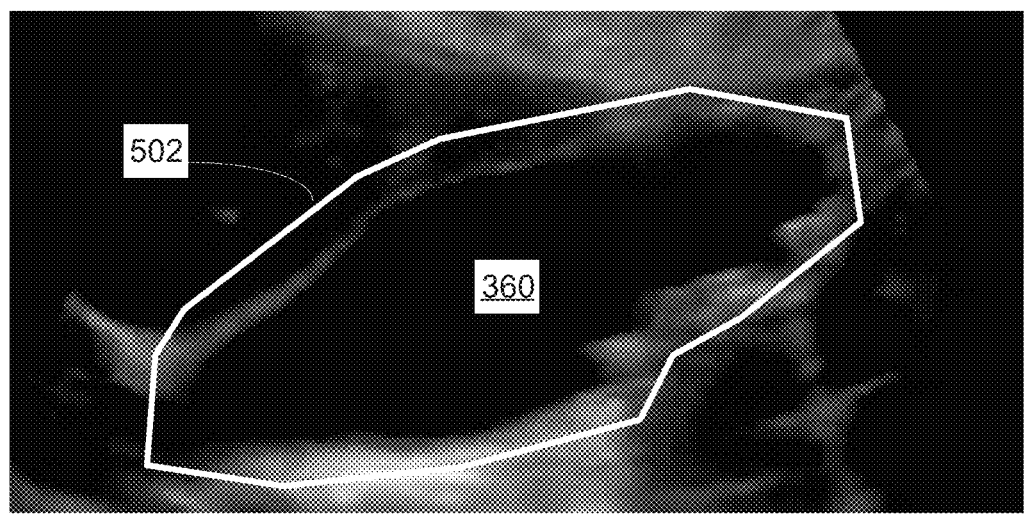
FIG. 5 illustrates the ultrasound image depicting the target feature, and a graphic on the image of an example of a shape drawn around the target feature.

FIG. 2 is a flow chart that illustrates an example of a process 200 for performing feature extraction on an ultrasound image, which can be performed on the ultrasound system illustrated in FIG. 1. The process 200 may include additional actions, in some embodiments fewer actions than is shown in the flowchart. At the beginning of the process 200, an ultrasound image can be displayed in a GUI on a touch screen interface, for example, the GUI illustrated in FIG. 3. At block 202, a feature in the ultrasound image can be identified. As an example, FIG. 4 illustrates an example of an ultrasound image that may be displayed on a touch-screen display that includes a target feature 360. In some embodiments, the system can suggest the presence of a feature using an automatic feature detection process. The system may also receive an input from a user of a point where the feature is located to identify the feature. For example, an input from a touchscreen indicating a point on the image where the feature is located. The system may also receive an input from a user of a portion of the image with the feature is located. For example, an input from a touchscreen indicating an area of the image in which the feature is located, the area having a free-form shape, or the shape of a circle, ellipse, a rectangle, or any other shape. FIG. 5 illustrates feature 360 having a shape 502 drawn around the feature 360 such that the feature 360 is within the shape 502.

Figure 6:
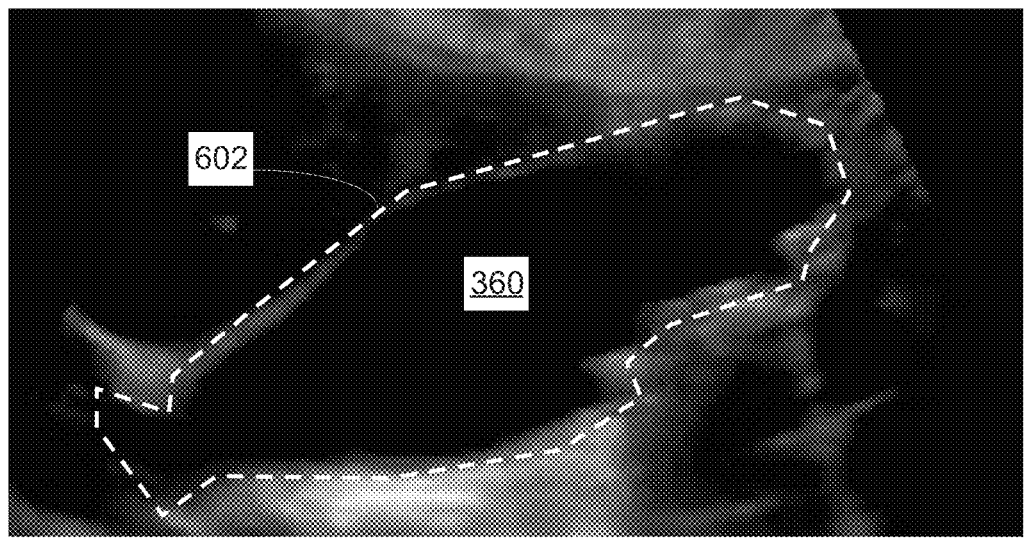
FIG. 6 illustrates the ultrasound image depicting the target feature, and a graphic on the image of an automatically generated boundary of the target feature.

At block 204, feature detection may be invoked to detect a feature based on the user input, and a graphical representation of an initial boundary of the feature may be generated. The feature detection methods used may include techniques of at detecting regions in an ultrasound image that differ in properties (e.g., pixel intensity), compared to surrounding regions. For example, the feature detection can be use one or more or intensity thresholding, Laplacian of the Gaussian, Informally, a feature is a region of an ultrasound image in which some properties are constant or approximately constant within a certain threshold or based on certain criteria. In other words, all the points in a feature can be considered in some sense to be similar to each other. FIG. 6 illustrates an initial boundary 602 that feature detection is generated around feature 360. At block 206, the initial boundary of the feature may be presented on the display for examination by the user to determine if the initial boundary is a satisfactory representation of the feature seen in the ultrasound image. At block 208, the user can adjust boundary 602 to be larger or smaller using a boundary adjustment control feature.

Figure 7:
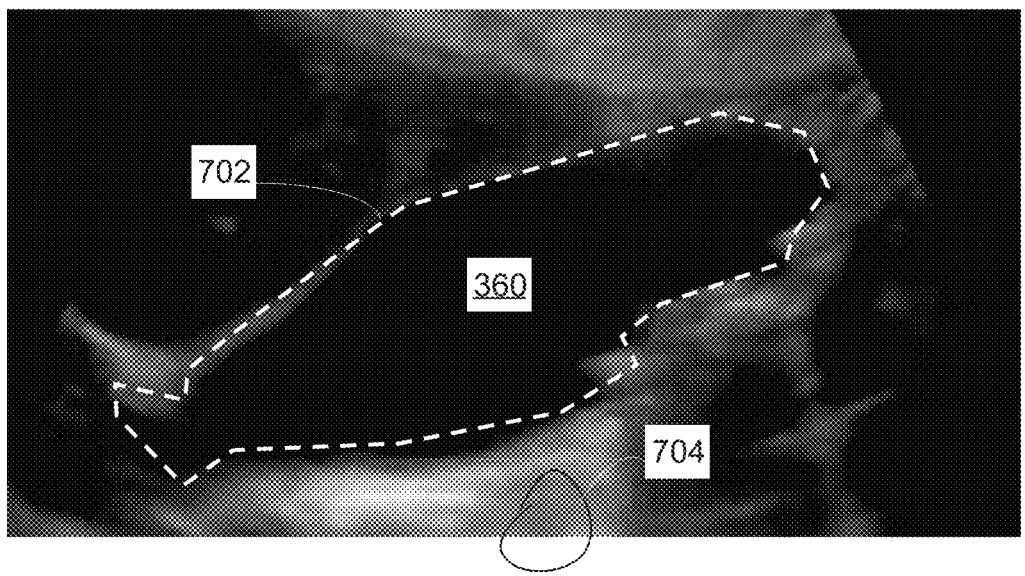
FIG. 7 illustrates the ultrasound image depicting the target feature, and graphics on the image of an automatically generated boundary of the target feature and an indicated location adjust a portion of the boundary.

One example of adjusting a boundary as illustrated in FIG. 7, where a user can provides input at a touchpoint 704, on the touchscreen displaying the ultrasound image, and the boundary 602 (FIG. 6) is moved away from, or towards the touchpoint. Here, touchpoint 704 causes a portion of the boundary 602 that is adjacent to the touchpoint 704 to move away from the location of the touchpoint 704 to form adjusted boundary 702. By providing similar input touchpoints on the touchscreen around the outside of boundary 602, the user can move boundary 602 "inward" away from the touchpoints. This can be done, for example, to form a better representation of the feature 360 when the boundary 602 extended past the perceived edge of the feature 360. Similarly, by providing inputs on the touchscreen around the inside of boundary 602, the user moves boundary 602 "outward" away from the touchpoints, expanding the size of the feature 360 to form adjusted boundary 702. This can be done to form a better representation of the feature 360 when the boundary 602 is inside the perceived edge of the feature 360. Alternatively, a similar process may be used to adjust the initial boundary such that the initial boundary is moved towards a touchpoint (instead of away from the touch point as described above).

Figure 8:
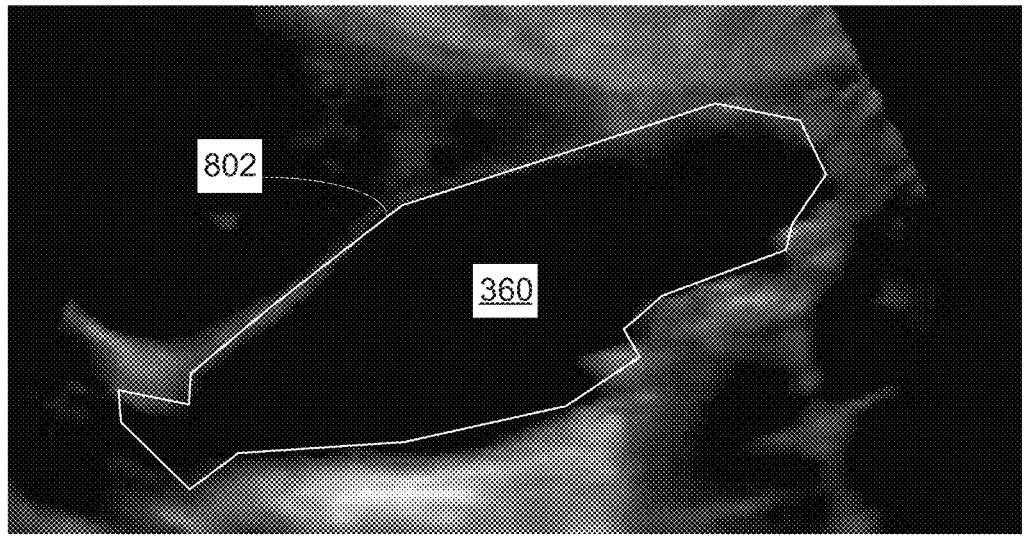
FIG. 8 illustrates the ultrasound image depicting the target feature, and a graphic on the image of a generated polygon based on the adjusted boundary.
Figure 9:
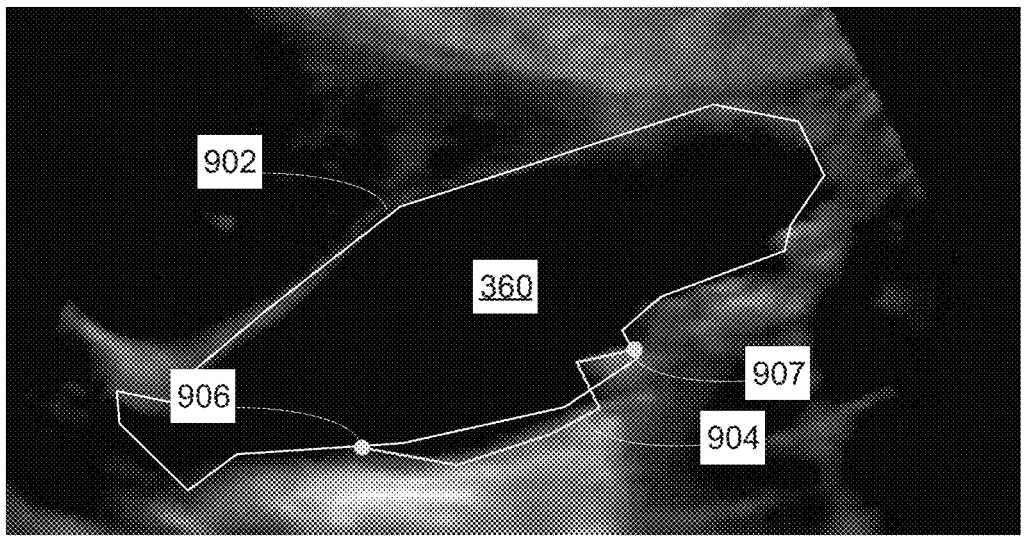
FIG. 9 illustrates the ultrasound image depicting the target feature, and a graphic on the image of illustrating editing of the polygon shown in FIG. 8.

At block 210, once the adjustment is complete the user can convert the boundary into a closed polygon 802, as illustrated in FIG. 8. When converting to the closed polygon, the line forming the polygon may be smoothed, using for example, cubic splines, by removing points on the polygon, or by another line smoothing technique.

At block 212, if desired the user can edit the polygon to further align the boundary of the polygon with the features seen in the ultrasound image, and/or to further align with expectations. In one example, editing the polygon is done by selecting (e.g., via the a touchscreen input) first point 906 on the polygon and then drawing a line 904 to a second point 907 on the polygon. The drawn line 904 will replace the part of the polygon between the two points. This can either increase or decrease the area polygon.

Figure 10:
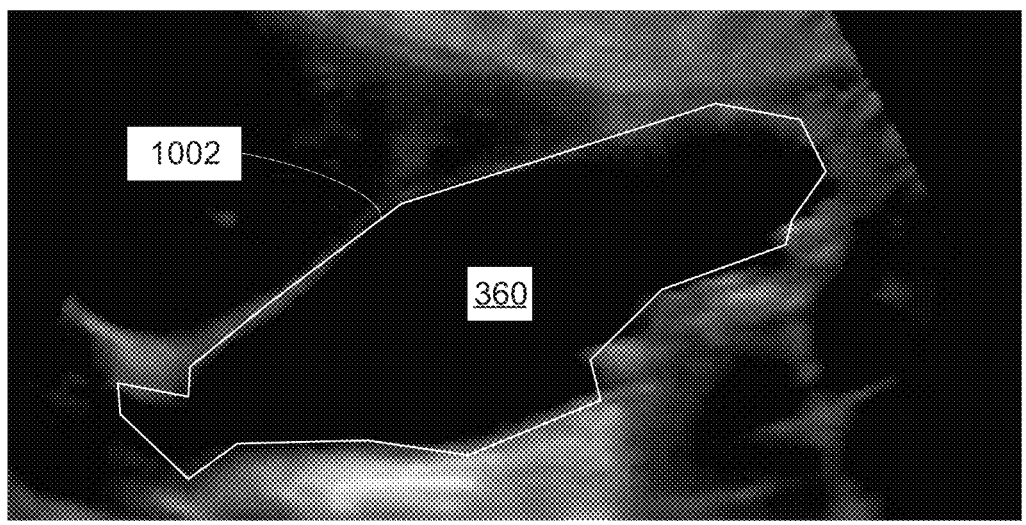
FIG. 10 illustrates the ultrasound image depicting the target feature, and a graphic on the image of illustrating a finalized polygon representing the target feature, which can be used to determine the area and perimeter of the target feature.

FIG. 10 illustrates the ultrasound image depicting the feature 360 and a graphic on the image of illustrating a finalized polygon 1002 representing the feature 360, which can be used to determine information relating to the area and perimeter of the feature 360. The finalized polygon 1002, determined information of the feature 360, and the underlying ultrasound image may be stored for future analysis. Also, in association may be formed between the finalized polygon 1002, determined information, and the underlying ultrasound image, and the association stored such that they can be easily referenced with each other. In one example, the finalized polygon 1002, determine information, and the underlying ultrasound image are stored in association with a visual protocol.

Figure 3:
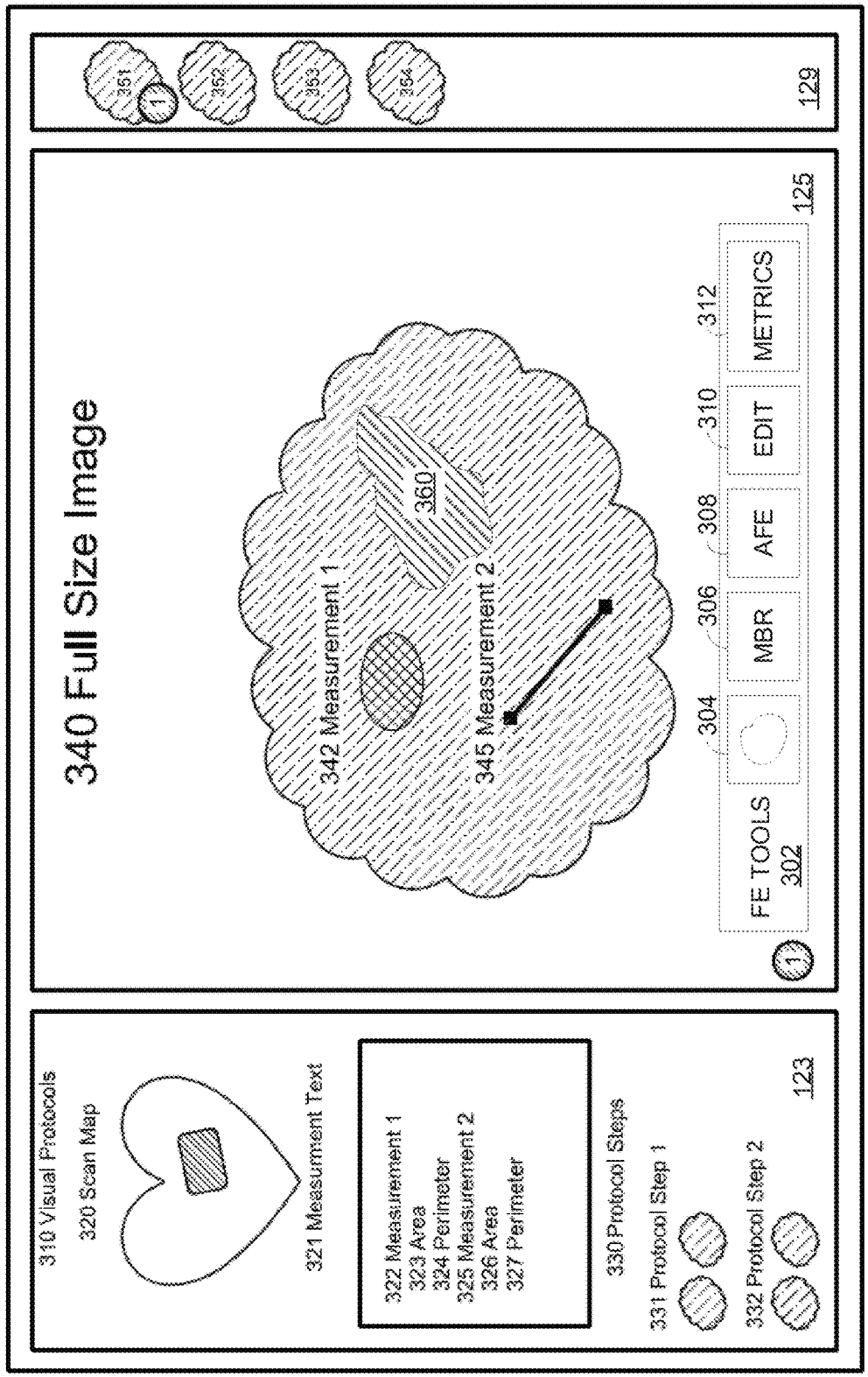
FIG. 3 is a diagram illustrating an example of a graphical user interface (GUI) that can be generated on a touch screen display, the GUI having panels that include tools for feature detection and extraction of a target feature.

FIG. 3 is a diagram illustrating an example of a graphical user interface (GUI) that can be generated on a touch screen display, the GUI having panels that include tools for feature detection and extraction of a target feature. In this example, the GUI includes a first panel 123 that is used to display information relating to a visual protocol been performed. The GUI also includes a second panel 125 that is used to display an ultrasound image that contains, for example, feature 360. The second panel 125 also includes feature extraction (FE) tools 302. A user may perform feature extraction the features found in the ultrasound image by touching the desired FE tool. In various embodiments, the FE tools 302 can include a number of FE tools. For example, a free-form selection tool 304, a minimum bounding rectangle selection tool 306, and an automatic feature extraction tool 308 they can be used, for example, to determine the boundary of a selected feature. The FE tools 302 can also include one or more edit tools 310 that a user can invoke to edit either in initially created boundary or a closed polygon. The FE tools 302 can also include metrics tool 312 that a user can invoke to determine metrics of the closed polygon, for example, the area of the polygon or the perimeter length of the polygon.

Figure 11:
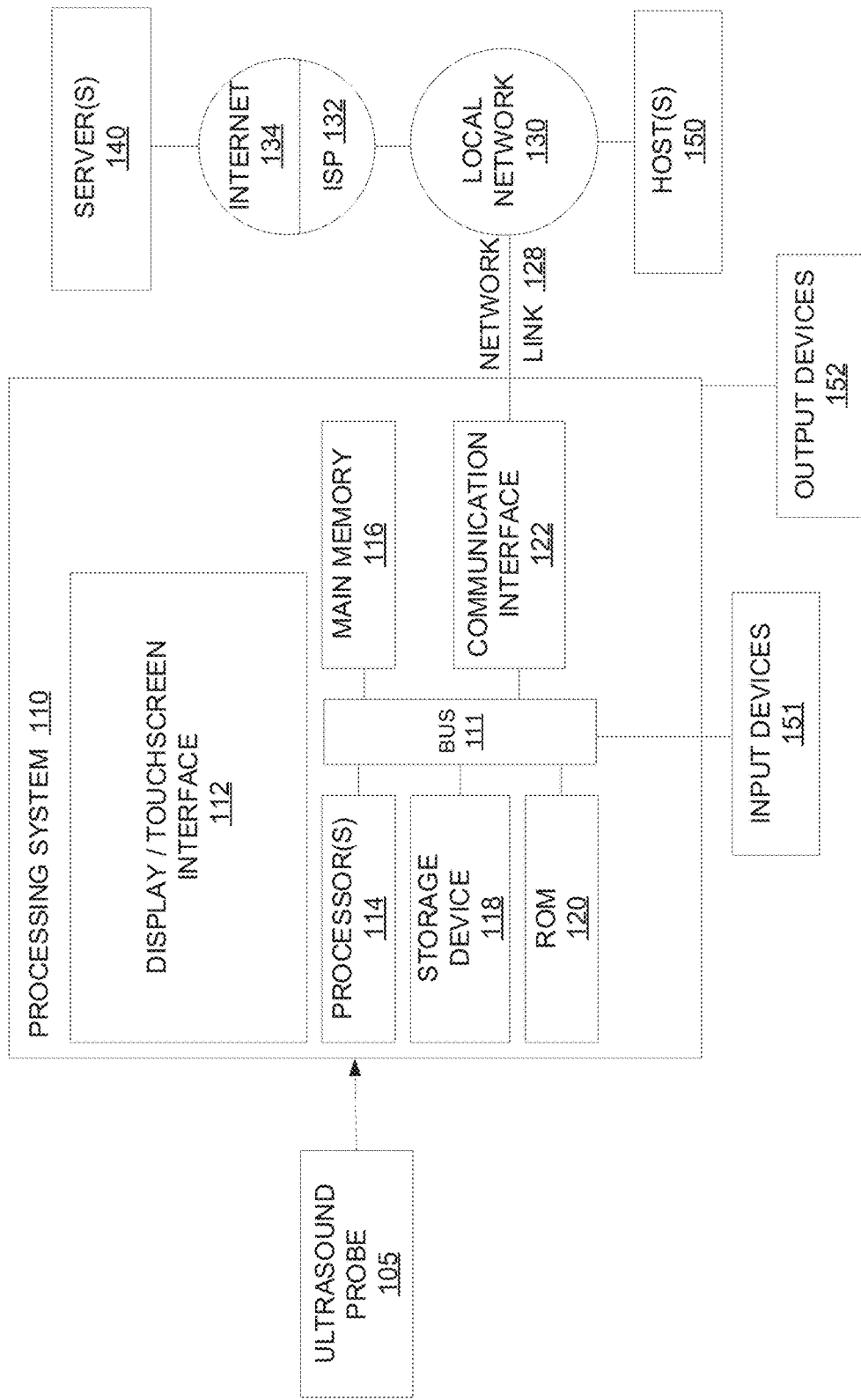
FIG. 11 is a block diagram illustrating an example of an ultrasound system that is adapted to perform functionality described herein.

FIG. 11 is a block diagram further illustrating an example of an ultrasound system 10 upon which various embodiments may be implemented. As illustrated in FIG. 1, the ultrasound system 10 includes an ultrasound probe 105 in communication with the processing system (computer system) 110. The ultrasound probe 105 can be connected to the computer system 110 via a wired or a wireless connection that allows the ultrasound probe 105 to provide ultrasound images to the computer system 110, and allows the ultrasound probe 105 to receive control signals from the computer system 110 the control signals indicating how ultrasound images should be collected.

The computer system 110 includes a bus 111 or other communication mechanism for communicating information, and a hardware processor (or multiple processors) 114 coupled with bus 111 for processing information. Hardware processor(s) 114 may be, for example, one or more general purpose microprocessors.

Computer system 110 also includes a main memory 116, such as a random access memory (RAM), cache and/or other dynamic storage devices, coupled to bus 111 for storing information and instructions to be executed by processor 114. Main memory 116 also may be used for storing temporary variables or other intermediate information during execution of instructions to be executed by processor 114. Such instructions, when stored in storage media accessible to processor 114, render computer system 110 into a special-purpose machine that is customized to perform the operations specified in the instructions. The main memory 116 may, for example, include instructions to allow a user detect and delineate graphical representations of features in ultrasound images, for example, as indicated in FIGS. 2-10.

Computer system 110 further includes a read only memory (ROM) 120 or other static storage device coupled to bus 111 for storing static information and instructions for processor 114. A storage device 118, such as a SSD drive, magnetic disk, optical disk, or USB thumb drive (Flash drive), etc., is provided and coupled to bus 111 for storing information and instructions.

Computer system 110 may be coupled via bus 111 to a display 112 (for example, a touch screen display) for displaying information to a computer user. One or more input devices 151 which may include alphanumeric and other keys and/or provide cursor control (e.g., mouse, trackball, or cursor direction keys) for communicating direction information and command selections to processor 114 and for controlling cursor movement on display 112 can be coupled to bus 111 for communicating information and command selections to processor 114.

Computer system 110 may include a user interface module to implement a GUI that may be stored in a mass storage device as computer executable program instructions that are executed by the computing device(s). Computer system 110 may further, as described below, implement the techniques described herein using customized hard-wired logic, one or more ASICs or FPGAs, firmware and/or program logic which in combination with the computer system causes or programs computer system 110 to be a special-purpose machine. According to one embodiment, the techniques herein are performed by computer system 110 in response to processor(s) 114 executing one or more sequences of one or more computer readable program instructions contained in main memory 116. Such instructions may be read into main memory 116 from another storage medium, such as storage device 118. Execution of the sequences of instructions contained in main memory 116 causes processor(s) 114 to perform the process steps described herein. In alternative embodiments, hard-wired circuitry may be used in place of or in combination with software instructions.

Various forms of computer readable storage media may be involved in carrying one or more sequences of one or more computer readable program instructions to processor 114 for execution. For example, the instructions may initially be carried on a magnetic disk or solid state drive of a remote computer. The remote computer can load the instructions into its dynamic memory and send the instructions over a network link 128. Bus 111 carries the data to main memory 116, from which processor 114 retrieves and executes the instructions. The instructions received by main memory 116 may optionally be stored on storage device 118 either before or after execution by processor 114.

Computer system 110 also includes a communication interface 122 coupled to bus 111. Communication interface 122 provides a two-way data communication coupling to the network link 128 that is connected to a local network 130. For example, communication interface 122 may be an integrated services digital network (ISDN) card, cable modem, satellite modem, or a modem to provide a data communication connection to a corresponding type of telephone line. As another example, communication interface 122 may be a local area network (LAN) card to provide a data communication connection to a compatible LAN (or WAN component to communicate with a WAN). Wireless links may also be implemented. In any such implementation, communication interface 122 sends and receives electrical, electromagnetic or optical signals that carry digital data streams representing various types of information.

Network link 128 typically provides data communication through one or more networks to other data devices. For example, network link 128 may provide a connection through local network 130 to a host computer 150 or to data equipment operated by an Internet Service Provider (ISP) 132. ISP 132 in turn provides data communication services through the world wide packet data communication network now commonly referred to as the "Internet" 134. Local network 130 and Internet 134 both use electrical, electromagnetic or optical signals that carry digital data streams. The signals through the various networks and the signals on network link 128 and through communication interface 122, which carry the digital data to and from computer system 110, are example forms of transmission media. Computer system 110 can send messages and receive data, including program code, through the network(s), network link 128 and communication interface 122. In the Internet example, a server 140 might transmit a requested code for an application program through Internet 134, ISP 132, local network 130, the network link 128, and communication interface 122. The received code may be executed by processor 114 as it is received, and/or stored in storage device 118, or other non-volatile storage for later execution.

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure. For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Implementation Considerations

References to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple one. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other.

"Logic" refers to machine memory circuits, non-transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter). Those skilled in the art will appreciate that logic may be distributed throughout one or more devices, and/or may be comprised of combinations of memory, media, processing circuits and controllers, other circuits, and so on. Therefore, in the interest of clarity and correctness logic may not always be distinctly illustrated in drawings of devices and systems, although it is inherently present therein.

The techniques and procedures described herein may be implemented via logic distributed in one or more computing devices. The particular distribution and choice of logic will vary according to implementation. Those having skill in the art will appreciate that there are various logic implementations by which processes and/or systems described herein can be effected (e.g., hardware, software, and/or firmware), and that the preferred vehicle will vary with the context in which the processes are deployed. "Software" refers to logic that may be readily readapted to different purposes (e.g. read/write volatile or nonvolatile memory or media). "Firmware" refers to logic embodied as read-only memories and/or media. Hardware refers to logic embodied as analog and/or digital circuits. If an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations may involve optically-oriented hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood as notorious by those within the art that each function and/or operation within such block diagrams, flowcharts, or examples can be implemented, individually and/or collectively, by a wide range of hardware, software, firmware, or virtually any combination thereof. Several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure.

In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory. In a general sense, those skilled in the art will recognize that the various aspects described herein which can be implemented, individually and/or collectively, by a wide range of hardware, software, firmware, or any combination thereof can be viewed as being composed of various types of "circuitry." Consequently, as used herein "circuitry" includes, but is not limited to, electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), circuitry forming a memory device (e.g., forms of random access memory), and/or circuitry forming a communications device (e.g., a modem, communications switch, or optical-electrical equipment).

One or more aspects or features of the subject matter disclosed or claimed herein (e.g., processes and methods) may be realized in digital electronic circuitry, integrated circuitry, specially designed application specific integrated circuits (ASICs), field programmable gate arrays (FPGAs) computer hardware, firmware, software, and/or combinations thereof. These various aspects or features may include implementation in one or more computer programs that may be executable and/or interpretable on a programmable system including at least one programmable processor, which may be special or general purpose, coupled to receive data and instructions from, and to transmit data and instructions to, a storage system, at least one input device, and at least one output device. The programmable system or computing system may include clients and servers. A client and server may be remote from each other and may interact through a communication network. The relationship of client and server arises by virtue of computer programs running on the respective computers and having a client-server relationship to each other.

These computer programs, which may also be referred to as programs, software, software applications, applications, components, or code, may include machine instructions for a programmable controller, processor, microprocessor or other computing or computerized architecture, and may be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium may store such machine instructions non-transitorily, such as for example as would a non-transient solid-state memory or a magnetic hard drive or any equivalent storage medium. The machine-readable medium may alternatively or additionally store such machine instructions in a transient manner, such as for example as would a processor cache or other random access memory associated with one or more physical processor cores.

In some embodiments, to provide for interaction with a user, one or more aspects or features of the subject matter described herein may be implemented on a computer having a display device for displaying information to the user, and an input interface by which the user may provide input to the computer. Other kinds of devices may be used to provide for interaction with a user as well. Other possible input devices include touch screens or other touch-sensitive devices such as single or multi-point resistive or capacitive trackpads, voice recognition hardware and software, and the like.

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure. For example, the functionality described herein may be performed as software instructions executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Computer readable program instructions, may as also referred to herein as, for example, "code," "instructions," "module," "application," "software application," and/or the like. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device.

Aspects of the present disclosure are described herein with reference to methods, apparatus (systems), and computer program products according to embodiments of the disclosure. It will be understood that each method can be implemented by computer readable program instructions. These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks. Any of the above-mentioned processors, and/or devices incorporating any of the above-mentioned processors, may be referred to herein as, for example, "computers," "computer devices," "computing devices," "hardware computing devices," "hardware processors," "processing units," and/or the like.

It will also be understood that, when a feature or element is referred to as being "connected", "attached" or "coupled" to another feature or element, it may be directly connected, attached or coupled to the other feature or element or intervening features or elements may be present. In contrast, when a feature or element is referred to as being "directly connected", "directly attached" or "directly coupled" to another feature or element, there may be no intervening features or elements present. Although described or shown with respect to one embodiment, the features and elements so described or shown may apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" may be intended to include the plural forms as well, unless the context clearly indicates otherwise. It will be further understood that the terms "comprises" and/or "comprising," when used in this specification, specify the presence of stated features, steps, operations, processes, functions, elements, and/or components, but do not preclude the presence or addition of one or more other features, steps, operations, processes, functions, elements, components, and/or groups thereof. As used herein, the term "and/or" includes any and all combinations of one or more of the associated listed items and may be abbreviated as "/".

The disclosed technology has been provided here with reference to one or more features or embodiments. Those skilled in the art will recognize and appreciate that, despite of the detailed nature of the example embodiments provided here, changes and modifications may be applied to said embodiments without limiting or departing from the generally intended scope. These and various other adaptations and combinations of the embodiments provided here are within the scope of the disclosed subject matter as defined by the disclosed elements and features and their full set of equivalents.

What is claimed is:

1. A method of displaying ultrasound images and detecting features of interest corresponding to the displayed ultrasound images using image processing techniques, the method comprising:
    storing computer-executable instructions and a set of ultrasound images on a non-transitory computer readable medium;
    displaying an ultrasound image including a feature of interest;
    determining a boundary of the feature of interest in the displayed ultrasound image;
    determining a closed polygon that represents the feature of interest based on the boundary,
    receiving user input indicating a first point and a second point on a border of the closed polygon, defining a new line between the first and second points, and replacing a portion of the closed polygon with the new line between the first and second points; and
    determining information of the feature of interest using dimensions of the closed polygon,
    wherein the method is performed by one or more computer hardware processors configured to execute computer-executable instructions stored on the non-transitory computer readable medium.

2. The method of claim 1, further comprising receiving user input indicative of a location of the feature of interest, wherein determining the boundary is based on the user input.

3. The method of claim 2, wherein receiving the user input indicative of the location of the feature of interest comprises receiving a signal from a touchscreen display, that is displaying the ultrasound image, as a result of a user touch of the touchscreen display.

4. The method of claim 2, wherein receiving the user input indicative of the location of the feature of interest comprises receiving a signal from one of a mouse, trackball, or a keyboard.

5. The method of claim 1, further comprising performing automatic feature detection on the ultrasound image to determine a location of the feature of interest, wherein determining the boundary is based on the determined location.

6. The method of claim 5, wherein the automatic feature detection is at least partially based on intensity of pixels in the ultrasound image.

7. The method of claim 6, further comprising adjusting the boundary by changing at least one of brightness or contrast of the displayed ultrasound image.

8. The method of claim 1, further comprising adjusting a portion of the boundary, based on user input, to form an adjusted boundary, and wherein determining the closed polygon that represents the feature of interest is based on the adjusted boundary.

9. The method of claim 8, wherein adjusting the portion of the boundary comprises receiving a signal, from a touchscreen displaying the ultrasound image and the boundary, indicative of a point on the ultrasound image, and adjusting the portion of the boundary adjacent to the point to move the boundary away from the point.

10. The method of claim 8, wherein adjusting the portion of the boundary comprises receiving a signal, from a touchscreen displaying the ultrasound image and the boundary, indicative of a point on the ultrasound image, and adjusting a portion of the boundary adjacent to the point to move the boundary towards the point.

11. The method of claim 1, further comprising smoothing the boundary.

12. The method of claim 11, wherein the boundary is smoothed using cubic splines or by removing points of the boundary.

13. The method of claim 1, further comprising smoothing the closed polygon.

14. The method of claim 13, wherein the closed polygon is smoothed using cubic splines or by removing points of the polygon.

15. The method of claim 1, wherein determining information of the feature using the dimensions of the closed polygon comprises determining one or more of an area of the closed polygon, a perimeter of the closed polygon, or a volume of the closed polygon.

16. The method of claim 1, further comprising generating a feature detection user interface comprising the ultrasound image and graphical representations, the graphical representations comprising the boundary and the closed polygon, and causing presentation of the feature detection user interface on a touchscreen display.

17. A system comprising:
an ultrasound probe;
an ultrasound processing system including a wireless network communication interface connecting the ultrasound probe to processing for receiving ultrasound data from the ultrasound probe and for providing control information to the ultrasound probe;
a first non-transitory computer storage medium configured to store the ultrasound data provided by the ultrasound probe;
second non-transitory computer storage medium configured to at least store computer-executable instructions; and
one or more computer hardware processors in communication with the second non-transitory computer storage medium, the one or more computer hardware processors configured to execute the computer-executable instructions to at least:
receive user input indicative of a location of a feature;
generate a feature detection user interface, the feature detection user interface comprising an ultrasound image and one or more graphical representations of the feature, and cause presentation of the feature detection user interface on a touchscreen display;
determine a boundary of the feature in a displayed ultrasound image based on the user input;
adjust the boundary based on user input indicative of moving a portion of the boundary;
determine a closed polygon that represents the feature based on the boundary;
edit the closed polygon based on user input indicating a first point of the closed polygon and a second point of the closed polygon, the first and second point defining a new line between the first point and the second point to replace the portion of the closed polygon between the first and second point with the new line between the first and second point; and
determine information of the feature using dimensions of the closed polygon.

18. The system of claim 17, wherein the determined information comprises at least one of an area of the closed polygon, a perimeter of the closed polygon, or a volume of the closed polygon, and wherein receiving user input indicative of the location of the feature comprises receiving a signal from the touchscreen display, that is displaying the ultrasound image, as a result of a user touch of the touchscreen.

* * * * *